US 11,083,889 B2

(12) United States Patent
Yang et al.

(10) Patent No.: US 11,083,889 B2
(45) Date of Patent: Aug. 10, 2021

(54) HELICAL FIXATION MEMBER ASSEMBLY HAVING BI-DIRECTIONAL CONTROLLED DRUG RELEASE

(71) Applicant: Medtronic, Inc., Minneapolis, MN (US)

(72) Inventors: Zhongping Yang, Woodbury, MN (US); Andrea Asleson, Maple Grove, MN (US); Gonzalo Martinez, Mendota Heights, MN (US); Rick D. McVenes, Isanti, MN (US); Christopher W. Storment, Sonoma, CA (US)

(73) Assignee: Medtronic, Inc., Minneapolis, MN (US)

( * ) Notice: Subject to any disclaimer, the term of this patent is extended or adjusted under 35 U.S.C. 154(b) by 607 days.

(21) Appl. No.: 15/884,636

(22) Filed: Jan. 31, 2018

(65) Prior Publication Data

US 2019/0232053 A1    Aug. 1, 2019

(51) Int. Cl.
*A61N 1/05* (2006.01)
*A61N 1/365* (2006.01)
*A61N 1/375* (2006.01)

(52) U.S. Cl.
CPC ........... *A61N 1/0575* (2013.01); *A61N 1/365* (2013.01); *A61N 1/3756* (2013.01); *A61N 1/37512* (2017.08)

(58) Field of Classification Search
CPC .. A61N 1/0575; A61N 1/37512; A61N 1/365; A61N 1/3756
See application file for complete search history.

(56) References Cited

U.S. PATENT DOCUMENTS

| 4,374,382 A | 2/1983 | Markowitz |
| 4,506,680 A | 3/1985 | Stokes |

(Continued)

OTHER PUBLICATIONS

Worthley et al., "First-in-Human Evaluation of a Novel Polymer Free Drug-Filled Stent: Angiographic, IVUS, OCT, and Clinical Outcomes from the RevElution Study," *JACC: Cardiovascular Interventions*, 2017; doi: 10.1016/j.jcin.2016.10.020. 10(2):1-46.

*Primary Examiner* — Carl H Layno
*Assistant Examiner* — Roland Dinga
(74) *Attorney, Agent, or Firm* — Mueting Raasch Group

(57) ABSTRACT

An implantable medical lead having an elongated lead body extending from a proximal end to a distal end, at least one conductor extending within the lead body from the proximal end to the distal end, and a fixation member having a proximal end and a distal end, the proximal end of the electrode configured to be electrically coupled to the distal end of the lead body. The fixation member includes a first delivery port and a second delivery port for releasing a therapeutic agent from the fixation member to tissue of a patient, wherein the first delivery port is positioned along the proximal end of the fixation member to deliver the therapeutic agent to endothelial cells along an endothelial layer of tissue, and the second delivery port is positioned along the distal end of the fixation member and spaced a distance from the first delivery port to deliver the therapeutic agent to myocardial tissue within a myocardial layer of the tissue, and wherein no delivery ports are positioned within the distance that the second delivery port is spaced from the first delivery port.

22 Claims, 10 Drawing Sheets

(56) References Cited

U.S. PATENT DOCUMENTS

| | | | |
|---|---|---|---|
| 4,606,118 | A | 8/1986 | Cannon et al. |
| 5,117,824 | A | 6/1992 | Keimel et al. |
| 5,489,294 | A | 2/1996 | McVenes et al. |
| 5,522,874 | A | 6/1996 | Gates |
| 5,545,186 | A | 8/1996 | Olson et al. |
| 5,755,736 | A | 5/1998 | Gillberg et al. |
| 6,567,705 | B1 * | 5/2003 | Stokes .................. A61M 37/00 607/120 |
| 7,953,499 | B2 | 5/2011 | Knapp et al. |
| 8,275,468 | B2 * | 9/2012 | Foster .................. A61N 1/0575 607/120 |
| 2003/0032998 | A1 | 2/2003 | Altman |
| 2009/0082828 | A1 * | 3/2009 | Ostroff ............... A61N 1/37512 607/36 |
| 2010/0004723 | A1 | 1/2010 | Foster et al. |
| 2010/0234930 | A1 | 9/2010 | Koop et al. |
| 2011/0125241 | A1 | 5/2011 | Cobian et al. |
| 2012/0109284 | A1 | 5/2012 | Caldarise et al. |
| 2014/0121720 | A1 | 5/2014 | Bonner et al. |
| 2018/0207433 | A1 * | 7/2018 | Koop .................. A61N 1/3756 |

\* cited by examiner

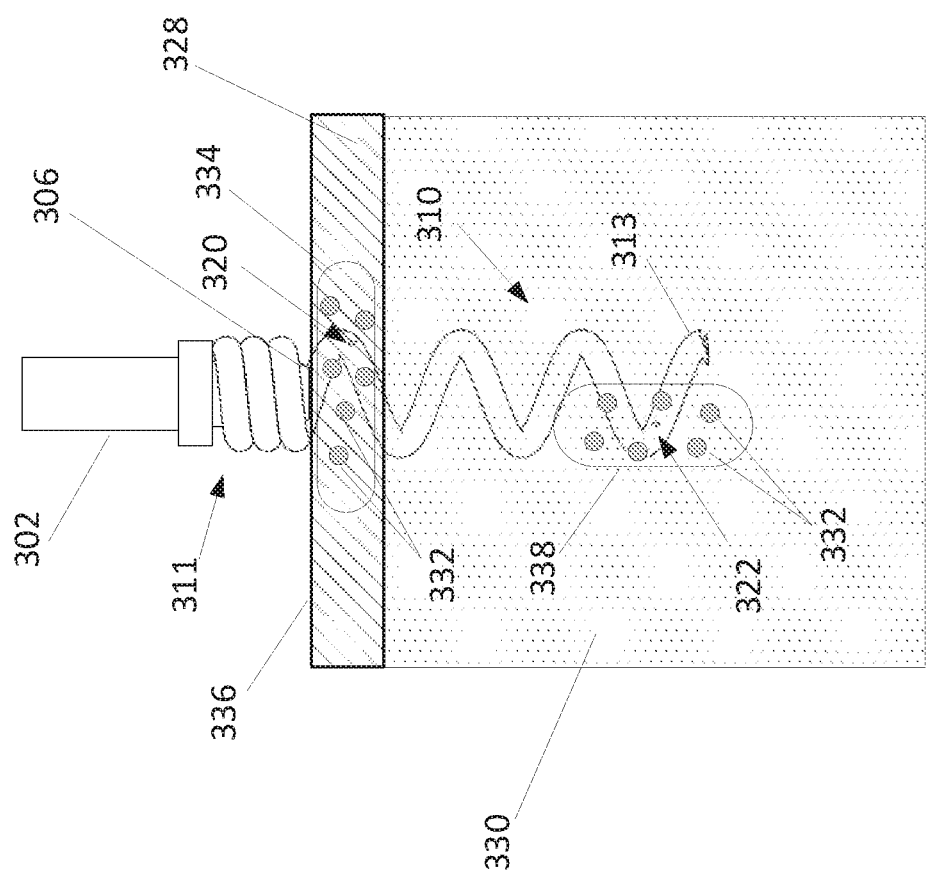
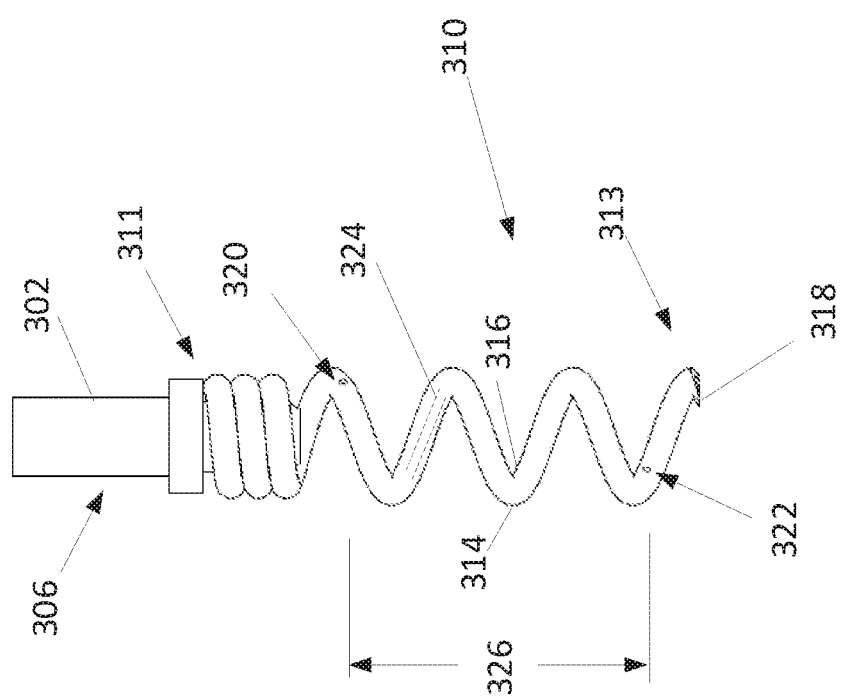
FIG. 8
FIG. 7

HELICAL FIXATION MEMBER ASSEMBLY HAVING BI-DIRECTIONAL CONTROLLED DRUG RELEASE

TECHNICAL FIELD

The present disclosure relates generally to cardiac medical devices, and more particularly to a method and apparatus for controlled release of a therapeutic agent within cardiac tissue surrounding an electrode of a cardiac medical device.

BACKGROUND

Implantable medical devices include a variety of devices that may provide monitoring of a physiological parameter of the patient, delivery of a therapy, such as electrical simulation therapy, to cardiac tissue of a patient, or both. For example, the implantable medical device delivers the electrical stimulation therapy and/or monitors physiological signals via one or more electrodes or sensor elements, which may be included on a housing of the device or as part of one or more elongated implantable medical leads. Implantable medical leads are configured to allow one or more electrodes and/or sensors to be positioned at desired locations for sensing or delivery of stimulation. For example, electrodes or sensors are positioned at a distal portion of the lead and a connector is positioned at a proximal portion of the lead and coupled to an implantable medical device housing, which may contain electronic circuitry such as stimulation generation and/or sensing circuitry.

In order to achieve cardiac pacing, sensing, cardioversion and/or defibrillation at different locations in the heart, various types of cardiac leads have been developed including epicardial leads, endocardial leads, and coronary vein leads. A transvenous endocardial lead establishes electrical contact between an electrical pulse generator, such as a pacemaker or implantable cardioverter defibrillator, and the endocardial surface of the heart, typically in a right heart chamber. Endocardial leads, and cardiac leads in general, may be held in place by passive fixation mechanisms, such as tines that interact with the ventricular trabeculae, or active fixation mechanisms, such as a helix located at the distal end of the lead. A coronary vein lead may be passed through a venous pathway, into the right atrium, through the coronary sinus ostium and ultimately to a location within the cardiac veins where the fixation mechanism is affixed to cardiac tissue.

In some examples, a leadless pacemaker may be used to sense electrical activity and/or deliver therapeutic signals to the heart. The leadless pacemaker may include one or more electrodes on its outer housing to deliver therapeutic electrical signals and/or sense intrinsic depolarizations of the heart. The leadless pacemaker may be positioned within or outside of the heart and, in some examples, may be anchored to a wall of the heart via a fixation mechanism.

Various properties of the lead, the electrodes and the tissue interfacing with an electrode will result in a characteristic impedance, stimulation threshold and sensing threshold. Stimulation threshold is the energy required in a stimulation pulse to depolarize, or "capture," the heart tissue. One factor that can affect the stimulation threshold, particularly during the first several weeks after implantation of a lead, is the natural immunological response of the body to the lead as a foreign object. The presence of the lead activates the immunologic response, which ultimately results in fibrotic encapsulation of the lead and its electrodes. Since fibrotic tissue is not excitable tissue, an elevated stimulation threshold can persist due to the degraded electrical properties of the electrode-tissue interface.

To reduce the inflammatory response, medical leads that elute an anti-inflammatory steroid have been developed. Steroid eluting leads may require a monolithic controlled release device (MCRD) to contain the steroid and to thereafter slowly leach out the water soluble steroid into the surrounding tissue. One limitation of a steroid eluting electrode or MCRD, however, is that a relatively limited volume of tissue is treated by the eluting drug since the drug is presented only at the endocardial surface. Other devices have been proposed in which a therapeutic agent stored within a luminal space of a helical fixation member is released through multiple elution ports located along the helical fixation member in fluid communication with the luminal space, which allows the delivery of the therapeutic agent directly within the tissue penetrated by and surrounding the helical fixation member. However, while current technology suggests that control of the release rate of the therapeutic agent may be accomplished by varying the number of elution ports that included along the electrode, increasing the number of elution ports increases the rate at which the agent is released, thereby reducing the length of time that the therapeutic agent is able to be delivered to the tissue. In addition, capillary filling of the device with the therapeutic agent becomes complicated when multiple elution ports are included on the fixation member. Therefore, improvements for enabling capillary filling of a helical fixation member with a therapeutic agent and long term control and targeted delivery of steroid elution from the helical fixation member are needed.

SUMMARY

In general, the disclosure is directed to providing long term control and targeted delivery of steroid elution from an electrode to tissue at an implant site. In one example, the disclosure is directed to an implantable medical lead, comprising: an elongated lead body extending from a proximal end to a distal end; a fixation member having a proximal end and a distal end, the proximal end of the fixation member configured to be electrically coupled to the distal end of the lead body, the helical fixation member comprising: a first delivery port and a second delivery port for releasing a therapeutic agent from the fixation member to tissue of a patient, wherein the first delivery port is positioned along the proximal end of the fixation member to deliver the therapeutic agent to endothelial cells along an endothelial layer of tissue, and the second delivery port is positioned along the distal end of the fixation member and spaced a distance from the first delivery port to deliver the therapeutic agent to myocardial tissue within a myocardial layer of the tissue, and wherein no delivery ports are positioned within the distance that the second delivery port is spaced from the first delivery port.

In another example, the disclosure is directed to an implantable medical device, comprising: a sensing module to sense a cardiac signal; a stimulation generator to deliver a cardiac therapy in response to the sensed cardiac signal; and a fixation member having a proximal end and a distal end, the proximal end of the helical fixation member configured to be electrically coupled to the distal end of the lead body, the helical fixation member comprising: a first delivery port and a second delivery port for releasing a therapeutic agent from the fixation member to tissue of a patient, wherein the first delivery port is positioned along the proximal end of the fixation member to deliver the therapeutic agent to endothelial cells along an endothelial layer of tissue, and the second delivery port is positioned along the distal end of the fixation member and spaced a distance from the first delivery port to deliver the therapeutic agent to myocardial tissue within a myocardial layer of the tissue, and wherein no delivery ports are positioned within the distance that the second delivery port is spaced from the first delivery port.

In another example, the disclosure is directed to a fixation member for use with an implantable medical device, the fixation member comprising: a helical body having a proximal end and a distal end and configured to be fixedly position within cardiac tissue; a lumen extending within the helical body and extending from the proximal end to the distal end; a first delivery port positioned along the proximal end of the helical body and in fluid communication with the lumen to deliver a therapeutic agent within the lumen to the cardiac tissue; and a second delivery port positioned along the distal end of the helical body and in fluid communication with the lumen to deliver the therapeutic agent to the cardiac tissue, the second delivery port spaced a distance from the first delivery port so that the therapeutic agent is delivered via the first delivery port to endothelial cells along an endothelial layer of the cardiac tissue, and the therapeutic agent is delivered via the second delivery port to myocardial tissue within a myocardial layer of the cardiac tissue, and wherein no delivery ports are positioned within the spaced distance between the first delivery port and the second delivery port.

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein:

FIG. 7 is a schematic diagram of a helical fixation member for controlled bi-directional delivery of a therapeutic agent, according to an example of the present disclosure.

FIG. 8 is a schematic diagram of a helical fixation member for controlled bi-directional delivery of a therapeutic agent, according to an example of the present disclosure.

DETAILED DESCRIPTION

Figure 1:
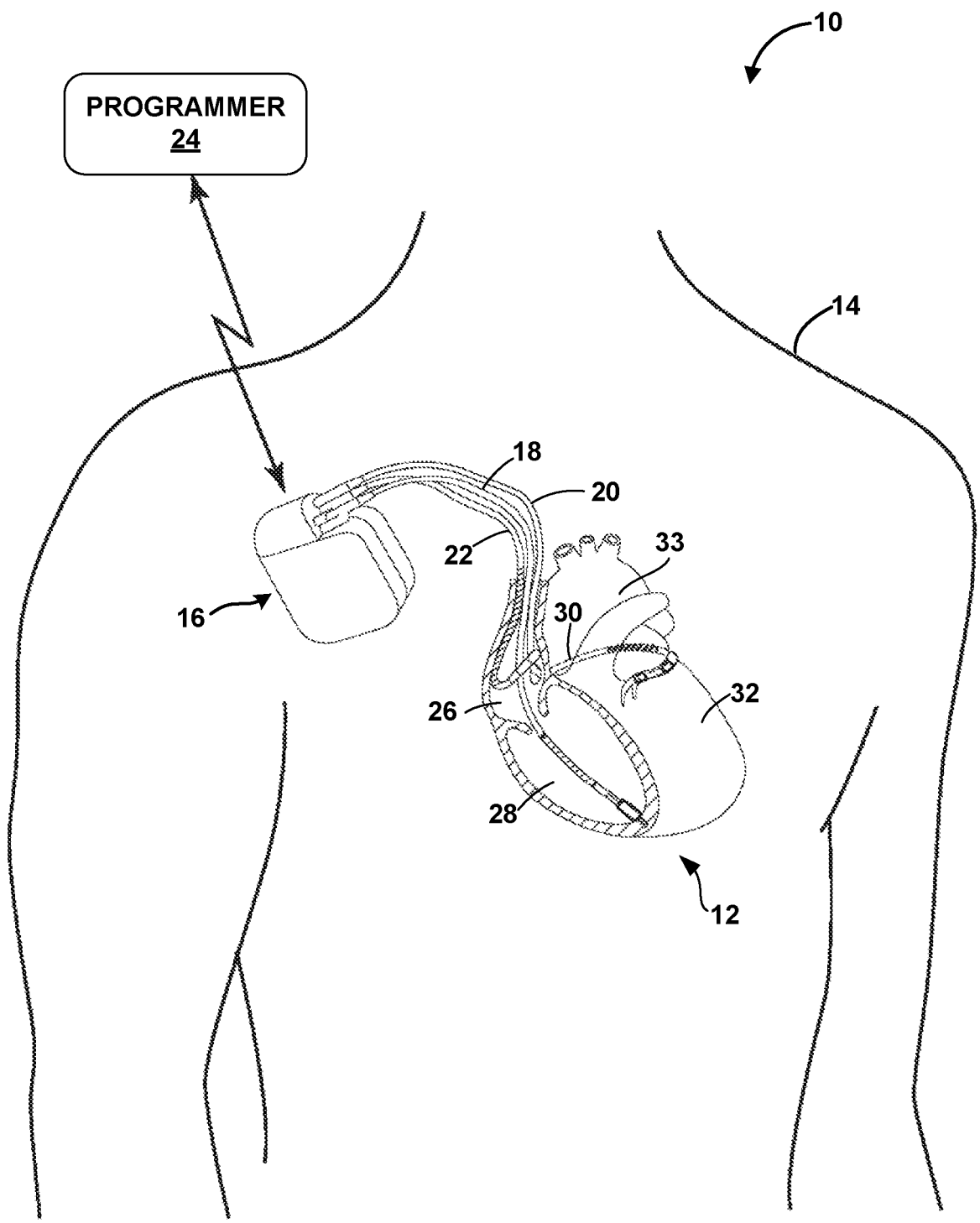
FIG. 1 is a conceptual diagram illustrating an example medical device system for delivering a therapeutic agent, consistent with an example of the present disclosure.

The techniques described in this disclosure provide improvements for providing long term control and targeted delivery of steroid elution and enabling capillary filling of a helical fixation member with a therapeutic agent. For example, an implantable medical device of the present disclosure includes a helical fixation member that includes a proximal delivery port and a distal delivery port, both of which are in fluid communication with a lumen within the helical fixation member that forms the inner diameter of the helical fixation member. In one example, both the proximal delivery port and the distal delivery port may have the same diameter, and thus release a therapeutic agent, such as a steroid, at approximately the same rate. However, in some examples, the diameters of the proximal delivery port and the distal delivery port may have different values, and thus release a therapeutic agent at different rates.

As a result, once the helical fixation member is fixated within tissue, such as cardiac tissue for example, a therapeutic agent, such as a steroid, may be bi-directionally released from the helical fixation member 310 within the cardiac tissue via the proximal delivery port 320 and the distal delivery port 322. More specifically, in order to enable a controlled bi-directional release of the therapeutic agent, the proximal delivery port is space a distance from the distal deliver port, with no additional deliver ports being positioned within the distance that the distal delivery port is spaced from the proximal delivery port.

According to an example of the present disclosure, the distance that the proximal delivery port of the electrode is spaced from the distal delivery port is configured so that the proximal delivery port of the helical fixation member is positioned within an endothelial layer of the tissue, and the distal delivery port is positioned within a layer of myocardial tissue below the endothelial layer.

As a result, the helical fixation member of the present disclosure enables a more targeted and controlled delivery of the therapeutic agent near a proximal electrode and/or a top surface of the cardiac tissue at the implant site and within the first fusion zone located within the endothelial layer of the tissue via the proximal delivery port. In addition, the therapeutic agent is delivered within a separate, second fusion zone located at the distal end of the helical electrode and within the myocardial tissue via the distal delivery port. Since the therapeutic agent is not delivered directly to the myocardial tissue along the space between the proximal delivery port and the distal delivery port, but rather is controlled so as to be delivered only within the first fusion zone and the second fusion zone, the present disclosure is configured to deliver the therapeutic agent using a more controlled, bi-directional release of the therapeutic agent.

In another example, the diameters of the proximal delivery port and the distal delivery port may have different values, enabling the amount of the therapeutic agent that is delivered via one delivery port to be different relative to the other port. For example, it may be desirable for the therapeutic agent to be delivered from the proximal delivery port at a rate greater than the amount delivered from the distal delivery port, resulting in more of the agent being delivered to the first fusion zone being greater than the amount of therapeutic agent delivered to the second fusion zone. Therefore, in this example the diameter of the proximal delivery port would be configured to be greater than the diameter of the distal delivery port. In another example, it may be desirable for the therapeutic agent to be delivered from the proximal delivery port at a rate less than the amount delivered from the distal delivery port, resulting in more of the agent being delivered to the second fusion zone being greater than the amount of therapeutic agent delivered to the first fusion zone. Therefore, in this example the diameter of the proximal delivery port would be configured to be less than the diameter of the distal delivery port.

By being configured to enable a more controlled, bi-directional release of a therapeutic agent, the present disclosure provides a more targeted and controlled approach to ensuring that the therapeutic agent is delivered to minimize the inflammatory response at specific targeted areas of tissue where inflammation is most likely to occur, such as within the endothelial layer of the tissue. By enabling delivery of the therapeutic agent to be controlled so as to be delivered within two separate specific fusion zones, the total fusion area may be reduced and more targeted, thereby minimizing the amount of the therapeutic agent that is delivered, extending the time period that the therapeutic agent continues to be released and enabling a more controlled and targeted reduction in the inflammation that may occur.

In addition, such controlled bi-directional release of the present disclosure minimizes corruption in the strength of the helical fixation member that would occur if the number of delivery ports is increased to be more than the two delivery ports described, thereby increasing the ability of the helical fixation member to more easily penetrate the tissue at the implant site, and further reducing the amount of inflammation that occurs at specific selected targeted problem areas of the implant site. Furthermore, by having only the proximal delivery port space the distance from the distal deliver port, with no delivery ports located within the distance between the proximal delivery port and the distal deliver port, the delivery of a therapeutic agent according to the present disclosure simplifies capillary filling of the helical fixation member.

FIG. 1 is a conceptual diagram illustrating an example implantable medical device system that may include bi-directionally controlled release of a therapeutic agent according to the present disclosure. As illustrated in FIG. 1, a system 10 having bi-directionally controlled release of a therapeutic agent according to the present disclosure may include an IMD 16, which is coupled to leads 18, 20, and 22, and a programmer 24. The IMD 16 may be, for example, an implantable pacemaker, cardioverter, and/or defibrillator that provides electrical signals to a heart 12 of a patient 16 via electrodes coupled to one or more of leads 18, 20, and 22.

Leads 18, 20, 22 extend into the heart 12 of the patient 16 to sense electrical activity of the heart 12 and/or deliver electrical stimulation to the heart 12. In the example shown in FIG. 1, right ventricular (RV) lead 18 extends through one or more veins (not shown), the superior vena cava (not shown), and a right atrium 26, and into a right ventricle 28. Left ventricular (LV) coronary sinus lead 20 extends through one or more veins, the vena cava, the right atrium 26, and into the coronary sinus 30 to a region adjacent to the free wall of a left ventricle 32 of the heart 12. Right atrial (RA) lead 22 extends through one or more veins and the vena cava, and into the right atrium 26 of heart 12.

IMD 16 may sense electrical signals attendant to the depolarization and repolarization of the heart 12 via electrodes (not shown in FIG. 1) coupled to at least one of the leads 18, 20, 22. In some examples, IMD 16 provides pacing pulses to the heart 12 based on the electrical signals sensed within the heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect an arrhythmia of the heart 12, such as fibrillation of the ventricles 28 and 32, and deliver defibrillation therapy to the heart 12 in the form of electrical pulses. In some examples, IMD 16 may be programmed to deliver a progression of therapies, e.g., pulses with increasing energy levels, until a fibrillation of the heart 12 is stopped. IMD 16 detects fibrillation employing one or more fibrillation detection techniques known in the art.

In some examples, a programmer 24 may be a handheld computing device or a computer workstation that can communicate with the IMD 16. The programmer 24 may include a user interface that receives input from a user, and that may include, for example, a keypad and a display, such as a cathode ray tube (CRT) display, a liquid crystal display (LCD) or light emitting diode (LED) display, for example. The keypad may take the form of an alphanumeric keypad or a reduced set of keys associated with particular functions. The programmer 24 may additionally or alternatively include a peripheral pointing device, such as a mouse, via which a user may interact with the user interface. In some embodiments, a display of the programmer 24 may include a touch screen display, and a user may interact with the programmer 24 via the display.

A user, such as a physician, technician, or other clinician, may interact with the programmer 24 to communicate with the IMD 16. For example, the user may interact with the programmer 24 to retrieve physiological or diagnostic information from the IMD 16. A user may also interact with the programmer 24 to program the IMD 16, e.g., select values for operational parameters of the IMD 16.

For example, the user may use the programmer 24 to retrieve information from the IMD 16 regarding the rhythm of the heart 12, trends therein over time, or tachyarrhythmia episodes. As another example, the user may use the programmer 24 to retrieve information from the IMD 16 regarding other sensed physiological parameters of the patient 14, such as intracardiac or intravascular pressure, activity, posture, respiration, or thoracic impedance. As another example, the user may use the programmer 24 to retrieve information from the IMD 16 regarding the performance or integrity of the IMD 16 or other components of the system 10, such as leads 18, 20, and 22, or a power source of the IMD 16.

The user may use the programmer 24 to program a therapy progression, select electrodes used to deliver defibrillation shocks, select waveforms for the defibrillation shock, or select or configure a fibrillation detection algorithm for the IMD 16. The user may also use the programmer 24 to program aspects of other therapies provided by the IMD 14, such as cardioversion or pacing therapies. In some examples, the user may activate certain features of the IMD 16 by entering a single command via the programmer 24, such as depression of a single key or combination of keys of a keypad or a single point-and-select action with a pointing device.

The IMD 16 and the programmer 24 may communicate via wireless communication using any techniques known in the art. Examples of communication techniques may include, for example, low frequency or radiofrequency (RF) telemetry, but other techniques are also contemplated. In some examples, the programmer 24 may include a programming head that may be placed proximate to the patient's body near the IMD 16 implant site in order to improve the quality or security of communication between the IMD 16 and the programmer 24.

Figure 2:
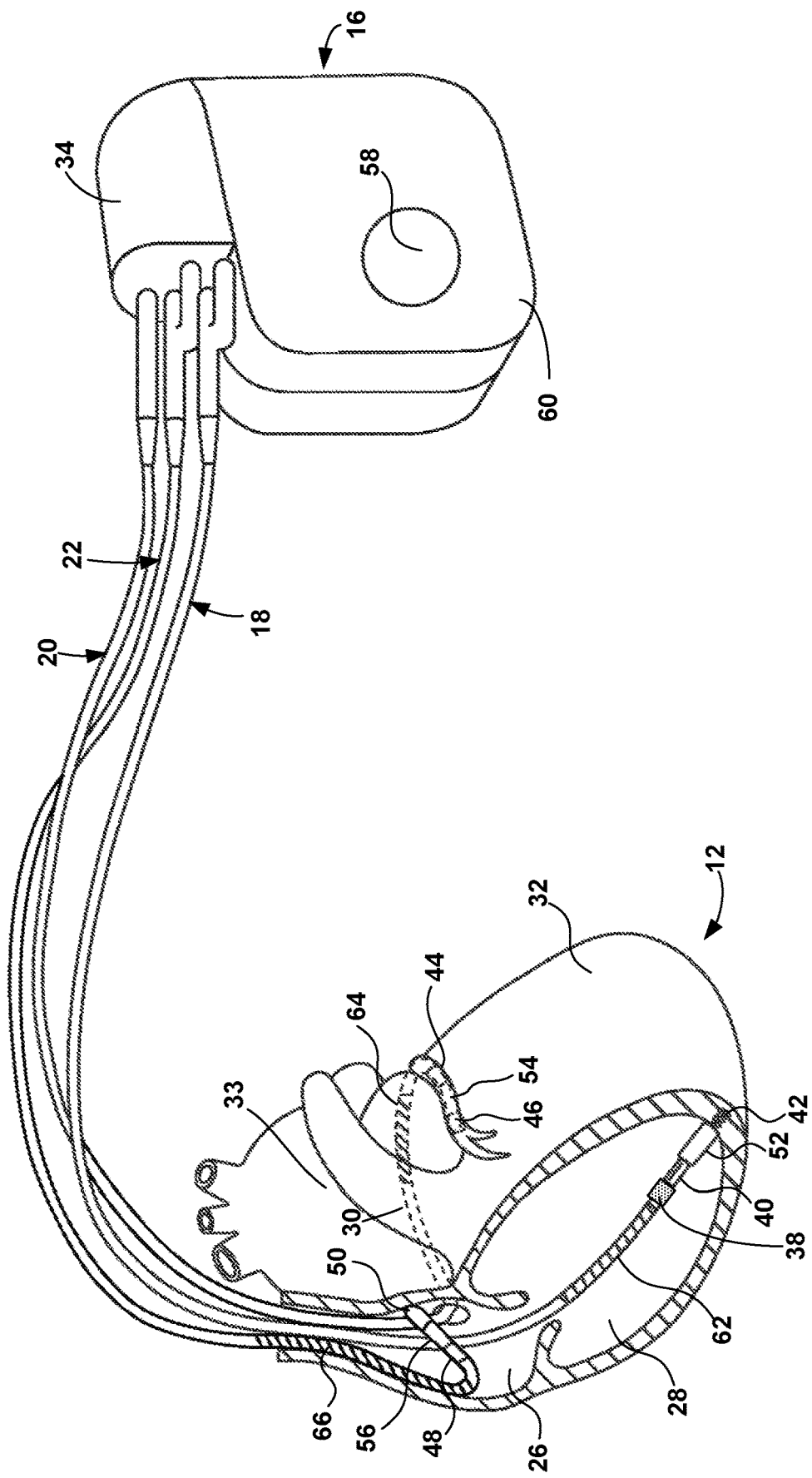
FIG. 2 is a conceptual diagram illustrating an implantable medical device (IMD) and leads of the system shown in FIG. 1 in greater detail.

FIG. 2 is a conceptual diagram illustrating an implantable medical device (IMD) and leads of the system shown in FIG. 1 in greater detail. As illustrated in FIG. 2, leads 18, 20, 22 may be electrically coupled to a stimulation generator, a sensing module, or other modules of IMD 16 via a connector block 34. In some examples, proximal ends of leads 18, 20, 22 may include electrical contacts that electrically couple to respective electrical contacts within the connector block 34. In addition, in some examples, leads 18, 20, 22 may be mechanically coupled to the connector block 34 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. In the illustrated example, a pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22.

Electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of the heart 12. The electrical signals are conducted to the IMD 16 via the respective leads 18, 20, 22. In some examples, the IMD 16 also delivers pacing pulses via electrodes 40, 42, 44, 46, 48 and 50 to cause depolarization of cardiac tissue of the heart 12. In some examples, as illustrated in FIG. 2, the IMD 16 includes one or more housing electrodes, such as housing electrode 58, which may be formed integrally with an outer surface of a hermetically-sealed housing 60 of the IMD 16 or otherwise coupled to the housing 60. In some examples, the housing electrode 58 is defined by an uninsulated portion of an outward facing portion of the housing 60 of the IMD 16. Other division between insulated and uninsulated portions of the housing 60 may be employed to define two or more housing electrodes. In some examples, housing electrode 58 comprises substantially all of the housing 60. Any of the electrodes 40, 42, 44, 46, 48 and 50 may be used for unipolar sensing or pacing in combination with the housing electrode 58. As described in further detail with reference to FIG. 4, the housing 60 may enclose a stimulation generator that generates cardiac pacing pulses and defibrillation or cardioversion shocks, as well as a sensing module for monitoring the patient's heart rhythm.

Leads 18, 20, 22 also include elongated electrodes 62, 64, 66, respectively, which may take the form of a coil. The IMD 16 may deliver defibrillation shocks to the heart 12 via any combination of elongated electrodes 62, 64, 66, and the housing electrode 58. Electrodes 58, 62, 64, 66 may also be used to deliver cardioversion pulses to the heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, the IMD 16 need not be implanted within the patient 14. In examples in which the IMD 16 is not implanted in the patient 14, the IMD 16 may deliver defibrillation shocks and other therapies to the heart 12 via percutaneous leads that extend through the skin of the patient 14 to a variety of positions within or outside of the heart 12.

In other examples of therapy systems that provide electrical stimulation therapy to the heart 12, a therapy system may include any suitable number of leads coupled to the IMD 16, and each of the leads may extend to any location within or proximate to the heart 12. For example, other examples of therapy systems may include three transvenous leads located as illustrated in FIGS. 1 and 2, and an additional lead located within or proximate to the left atrium 33. As another example, other examples of therapy systems may include a single lead that extends from the IMD 16 into the right atrium 26 or the right ventricle 28, or two leads that extend into a respective one of the right ventricle 26 and right atrium 28. An example of this type of therapy system is shown in FIG. 3.

Figure 3:
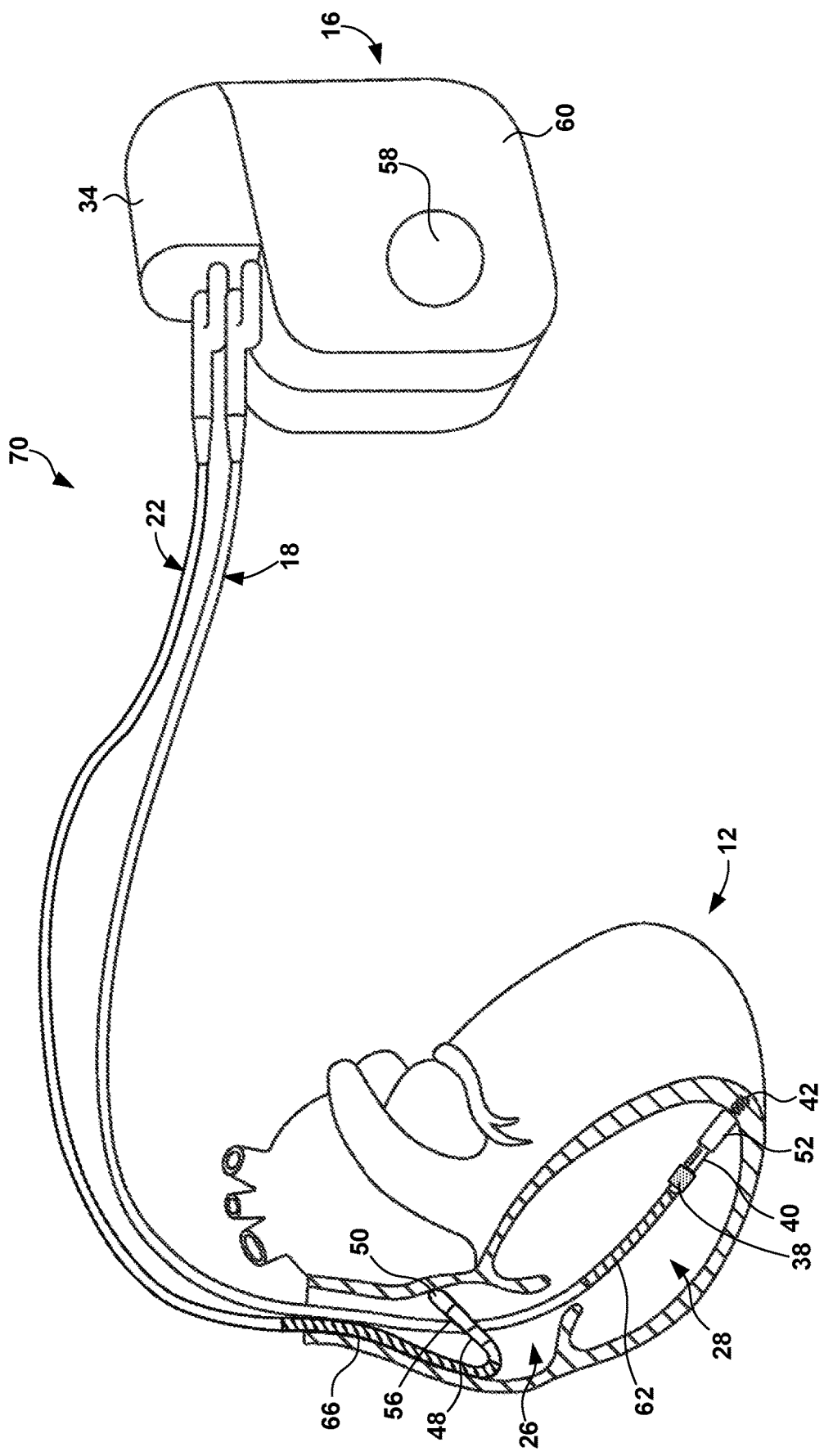
FIG. 3 is a conceptual diagram illustrating another example of medical device system, which is similar to system of FIGS. 1-2, but includes two leads, rather than three leads.

FIG. 3 is a conceptual diagram illustrating another example of a medical device system, which is similar to system of FIGS. 1-2, but includes two leads, rather than three leads. As illustrated in FIG. 3 a medical device system 70 that may include bi-directionally controlled release of a therapeutic agent according to the present disclosure may include only leads 18, 22 that are implanted within the right ventricle 28 and the right atrium 26, respectively. The exemplary medical device system 70 shown in FIG. 3 may be useful for providing defibrillation and pacing pulses to the heart 12.

Figure 4:
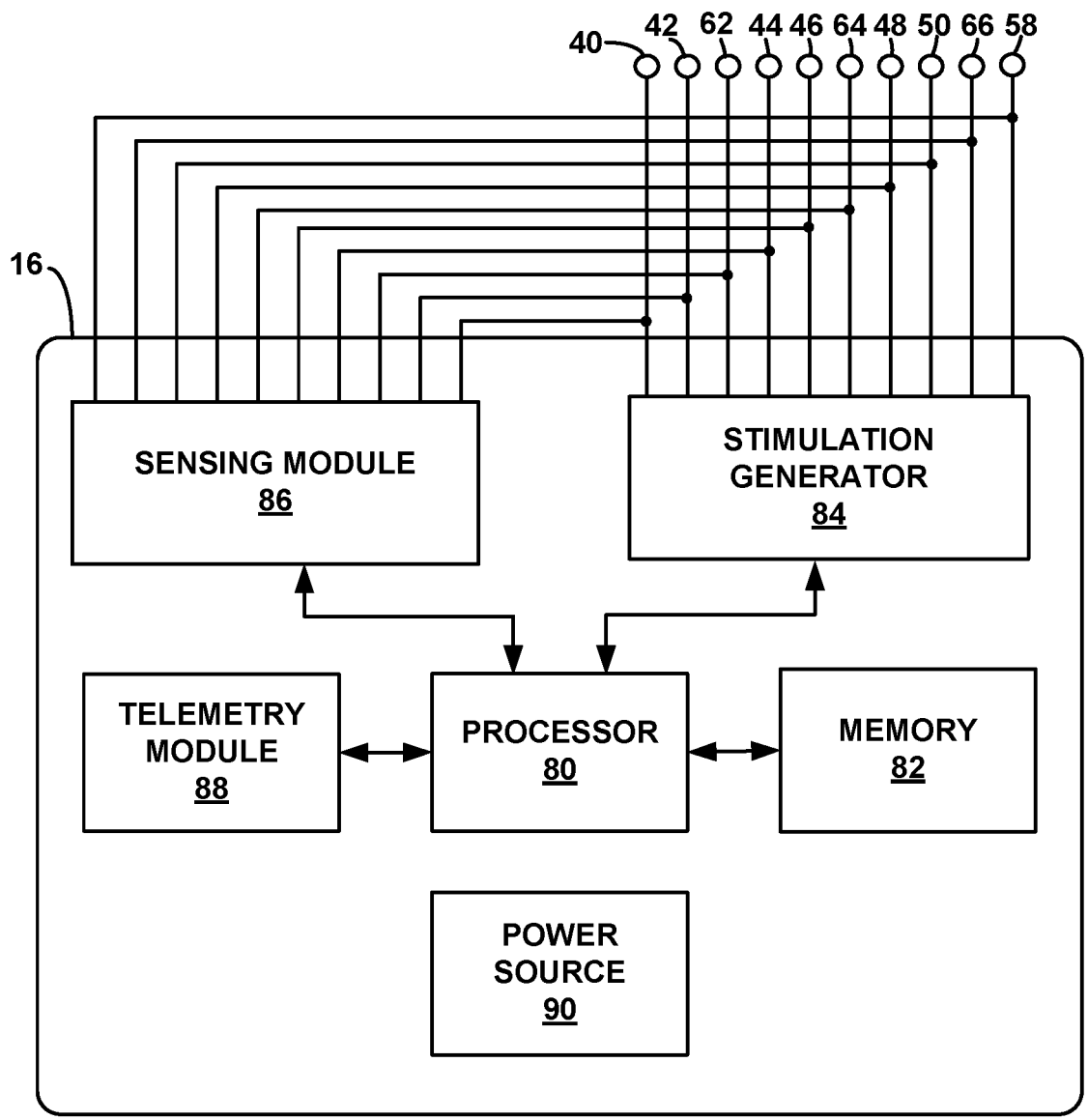
FIG. 4 is a functional block diagram of one example configuration of an IMD according to an example of the present disclosure.

FIG. 4 is a functional block diagram of an example configuration of an example implantable medical device according to the present disclosure. As illustrated in FIG. 4, according to an example of the present disclosure, the IMD 16 may include a processor 80, a memory 82, a stimulation generator 84, a sensing module 86, a telemetry module 88, and a power source 90. The memory 82 includes computer-readable instructions that, when executed by the processor 80, cause the IMD 16 and the processor 80 to perform various functions attributed to the IMD 16 and the processor 80 described herein. The memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, the processor 80 may include multiple components, such as any combination of one or more microprocessors, one or more controllers, one or more DSPs, one or more ASICs, or one or more FPGAs, as well as other discrete or integrated logic circuitry. The functions attributed to the processor 80 herein may be embodied as software, firmware, hardware or any combination thereof. The processor 80 controls the stimulation generator 84 to deliver stimulation therapy to the heart 12 according to a selected one or more of therapy programs, which may be stored in the memory 82. Specifically, the processor 44 may control the stimulation generator 84 to deliver electrical pulses with the amplitudes, pulse widths, frequency, or electrode polarities specified by the selected one or more therapy programs.

The stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within the housing 60 of the IMD 16. The stimulation generator 84 may be configured to generate and deliver electrical stimulation therapy to the heart 12. For example, the stimulation generator 84 may deliver defibrillation shocks to the heart 12 via at least two electrodes 58, 62, 64, 66. The stimulation generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, the stimulation generator 84 delivers pacing, cardioversion, or defibrillation stimulation in the form of electrical pulses. In other examples, the stimulation generator 84 may deliver one or more of these types of stimulation in the form of other signals, such as sine waves, square waves, or other substantially continuous time signals.

The stimulation generator 84 may include a switch module, and the processor 80 may use the switch module to select, e.g., via a data/address bus, which of the available electrodes are used to deliver defibrillation shocks or pacing pulses. The switch module may include a switch array, switch matrix, multiplexer, or any other type of switching device suitable to selectively couple stimulation energy to selected electrodes.

The sensing module 86 monitors signals from at least one of electrodes 40, 42, 44, 46, 48, 50, 58, 62, 64 or 66 in order to monitor electrical activity of the heart 12, e.g., via electrocardiogram (ECG) signals. The sensing module 86 may also include a switch module to select which of the available electrodes are used to sense the heart activity. In some examples, the processor 80 may select the electrodes that function as sense electrodes via the switch module within the sensing module 86, e.g., by providing signals via a data/address bus. In some examples, the sensing module 86 includes one or more sensing channels, each of which may comprises an amplifier. In response to the signals from the processor 80, the switch module of within the sensing module 86 may couple the outputs from the selected electrodes to one of the sensing channels.

In some examples, one channel of the sensing module 86 may include an R-wave amplifier that receives signals from electrodes 40 and 42, which are used for pacing and sensing in the right ventricle 28 of the heart 12. Another channel may include another R-wave amplifier that receives signals from electrodes 44 and 46, which are used for pacing and sensing proximate to the left ventricle 32 of the heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of the sensing module 86 may include a P-wave amplifier that receives signals from electrodes 48 and 50, which are used for pacing and sensing in the right atrium 26 of the heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of the sensing module 86 may be selectively coupled to the housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of the heart 12.

In some examples, the sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in the memory 82 as an electrogram (EGM). In some examples, the storage of such EGMs in the memory 82 may be under the control of a direct memory access circuit. The processor 80 may employ digital signal analysis techniques to characterize the digitized signals stored in the memory 82 to detect and classify the patient's heart rhythm from the electrical signals. The processor 80 may detect and classify the heart rhythm of the patient 14 by employing any of the numerous signal processing methodologies known in the art.

If the IMD 16 is configured to generate and deliver pacing pulses to the heart 12, the processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of the processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from the sensing module 86 to blank one or more channels, e.g., amplifiers, for a period during and after delivery of electrical stimulation to the heart 12. The durations of these intervals may be determined by the processor 80 in response to stored data in the memory 82. The pacer timing and control module of the processor 80 may also determine the amplitude of the cardiac pacing pulses.

During pacing, escape interval counters within the pacer timing/control module of the processor 80 may be reset upon sensing of R-waves and P-waves. The stimulation generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of the heart 12. The processor 80 may reset the escape interval counters upon the generation of pacing pulses by the stimulation generator 84, and thereby control the basic timing of cardiac pacing functions, including anti-tachyarrhythmia pacing.

The value of the count present in the escape interval counters when reset by sensed R-waves and P-waves may be used by the processor 80 to measure the durations of R-R intervals, P-P intervals, P-R intervals and R-P intervals, which are measurements that may be stored in memory 82. The processor 80 may use the count in the interval counters to detect a tachyarrhythmia event, such as ventricular fibrillation event or ventricular tachycardia event. Upon detecting a threshold number of tachyarrhythmia events, the processor 80 may identify the presence of a tachyarrhythmia episode, such as a ventricular fibrillation episode, a ventricular tachycardia episode, or a non-sustained tachycardia (NST) episode.

In some examples, the processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by the processor 80 and any updating of the values or intervals controlled by the pacer timing and control module of the processor 80 may take place following such interrupts. A portion of the memory 82 may be configured as a plurality of recirculating buffers, capable of holding series of measured intervals, which may be analyzed by the processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND GREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 80 in other examples.

In the examples described herein, the processor 80 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within the memory 82 of the IMB 16. In addition, the number of tachyarrhythmia events that are detected to confirm the presence of a tachyarrhythmia episode may be stored as a number of intervals to detect (NID) threshold value in memory 82. In some examples, the processor 80 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, the processor 80 may determine that the tachyarrhythmia is present.

If the processor 80 detects an atrial or ventricular tachyarrhythmia based on signals from the sensing module 86, and an anti-tachyarrhythmia pacing regimen is desired, timing intervals for controlling the generation of anti-tachyarrhythmia pacing therapies by the stimulation generator 84 may be loaded by the processor 80 into the pacer timing and control module to control the operation of the escape interval counters therein and to define refractory periods during which detection of R-waves and P-waves is ineffective to restart the escape interval counters.

If the IMD 16 is configured to generate and deliver defibrillation shocks to the heart 12, the stimulation generator 84 may include a high voltage charge circuit and a high voltage output circuit. In the event that generation of a cardioversion or defibrillation shock is required, the processor 80 may employ the escape interval counter to control timing of such cardioversion and defibrillation shocks, as well as associated refractory periods. In response to the detection of atrial or ventricular fibrillation or tachyarrhythmia requiring a cardioversion pulse, the processor 80 may activate a cardioversion/defibrillation control module, which may, like pacer timing and control module, be a hardware component of the processor 80 and/or a firmware or software module executed by one or more hardware components of the processor 80. The cardioversion/defibrillation control module may initiate charging of the high voltage capacitors of the high voltage charge circuit of the stimulation generator 84 under control of a high voltage charging control line.

The processor 80 may monitor the voltage on the high voltage capacitor, e.g., via a voltage charging and potential (VCAP) line. In response to the voltage on the high voltage capacitor reaching a predetermined value set by the processor 80, the processor 80 may generate a logic signal that terminates charging. Thereafter, timing of the delivery of the defibrillation or cardioversion pulse by the stimulation generator 84 is controlled by the cardioversion/defibrillation control module of the processor 80. Following delivery of the fibrillation or tachycardia therapy, the processor 80 may return the stimulation generator 84 to a cardiac pacing function and await the next successive interrupt due to pacing or the occurrence of a sensed atrial or ventricular depolarization.

The stimulation generator 84 may deliver cardioversion or defibrillation shocks with the aid of an output circuit that determines whether a monophasic or biphasic pulse is delivered, whether the housing electrode 58 serves as cathode or anode, and which electrodes are involved in delivery of the cardioversion or defibrillation shocks. Such functionality may be provided by one or more switches or a switching module of the stimulation generator 84.

The telemetry module 88 includes any suitable hardware, firmware, software or any combination thereof for communicating with another device, such as the programmer 24 (FIG. 1). Under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer.

In some examples, the processor 80 may transmit atrial and ventricular heart signals (e.g., electrocardiogram signals) produced by atrial and ventricular sense amp circuits within the sensing module 86 to the programmer 24. The programmer 24 may interrogate the IMB 16 to receive the heart signals. The processor 80 may store heart signals within the memory 82, and retrieve stored heart signals from the memory 82. The processor 80 may also generate and store marker codes indicative of different cardiac episodes that the sensing module 86 detects, and transmit the marker codes to the programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of the IMB 16 are coupled to the power source 90, which may include a rechargeable or non-rechargeable battery. A non-rechargeable battery may be selected to last for several years, while a rechargeable battery may be inductively charged from an external device, e.g., on a daily or weekly basis.

Figure 5:
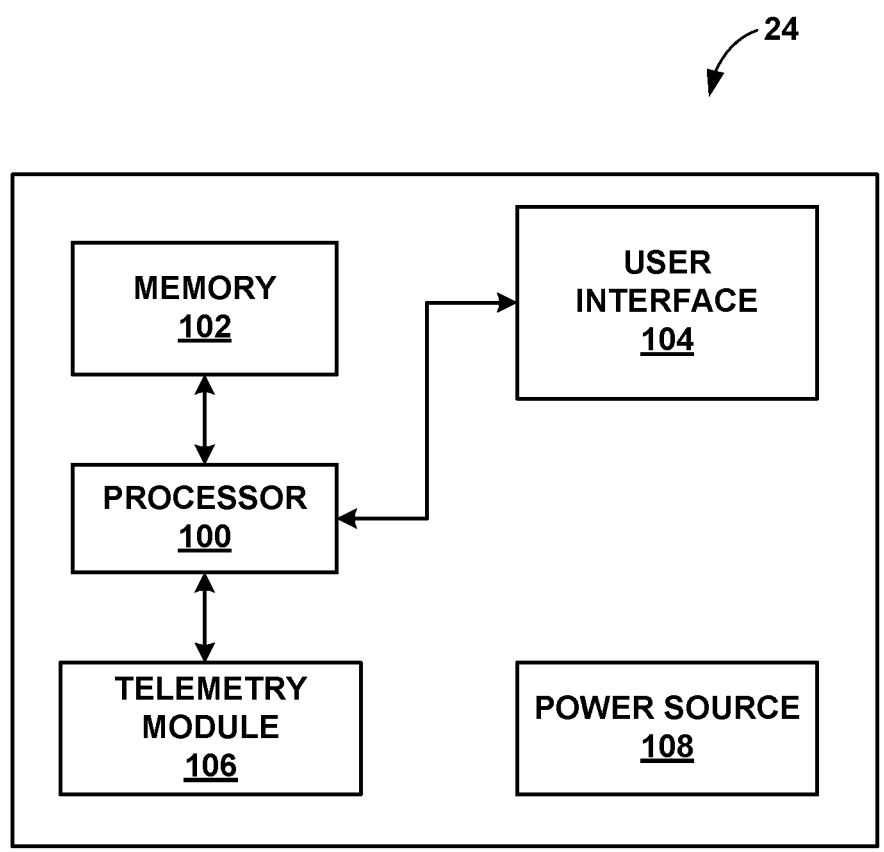
FIG. 5 is a functional block diagram of one example configuration of a programmer according to an example of the present disclosure.

FIG. 5 is a functional block diagram of one example configuration of a programmer according to an example of the present disclosure. As illustrated in FIG. 5, according to one example, the programmer 24 may include a processor 100, a memory 102, a user interface 104, a telemetry module 106, and a power source 108. The programmer 24 may be a dedicated hardware device with dedicated software for programming of the IMD 16. Alternatively, the programmer 24 may be an off-the-shelf computing device running an application that enables the programmer 24 to program the IMB 16.

A user may use the programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with the programmer 24 via the user interface 104, which may include display to present graphical user interface to a user, and a keypad or another mechanism for receiving input from a user.

The processor 100 can take the form one or more microprocessors, DSPs, ASICs, FPGAs, programmable logic circuitry, or the like, and the functions attributed to the processor 100 herein may be embodied as hardware, firmware, software or any combination thereof. The memory 102 may store instructions that cause the processor 100 to provide the functionality ascribed to the programmer 24 herein, and information used by the processor 100 to provide the functionality ascribed to the programmer 24 herein. The memory 102 may include any fixed or removable magnetic, optical, or electrical media, such as RAM, ROM, CD-ROM, hard or floppy magnetic disks, EEPROM, or the like. The memory 102 may also include a removable memory portion that may be used to provide memory updates or increases in memory capacities. A removable memory may also allow patient data to be easily transferred to another computing device, or to be removed before the programmer 24 is used to program therapy for another patient. The memory 102 may also store information that controls therapy delivery by the IMD 16, such as stimulation parameter values.

The programmer 24 may communicate wirelessly with the IMD 16, such as using RF communication or proximal inductive interaction. This wireless communication is possible through the use of the telemetry module 102, which may be coupled to an internal antenna or an external antenna. An external antenna that is coupled to the programmer 24 may correspond to the programming head that may be placed over the heart 12, as described above with reference to FIG. 1. The telemetry module 102 may be similar to the telemetry module 88 of the IMD 16 (FIG. 4).

The telemetry module 102 may also be configured to communicate with another computing device via wireless communication techniques, or direct communication through a wired connection. Examples of local wireless communication techniques that may be employed to facilitate communication between the programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with the programmer 24 without needing to establish a secure wireless connection.

The power source 108 delivers operating power to the components of the programmer 24, and may include a battery and a power generation circuit to produce the operating power. In some embodiments, the battery may be rechargeable to allow extended operation. Recharging may be accomplished by electrically coupling the power source 108 to a cradle or plug that is connected to an alternating current (AC) outlet. In addition or alternatively, recharging may be accomplished through proximal inductive interaction between an external charger and an inductive charging coil within the programmer 24. In other embodiments, traditional batteries (e.g., nickel cadmium or lithium ion batteries) may be used. In addition, the programmer 24 may be directly coupled to an alternating current outlet to power the programmer 24. The power source 104 may include circuitry to monitor power remaining within a battery. In this manner, the user interface 104 may provide a current battery level indicator or low battery level indicator when the battery needs to be replaced or recharged. In some cases, the power source 108 may be capable of estimating the remaining time of operation using the current battery.

Referring again to FIG. 4, the processor 80 of the IMD 16 may detect a tachyarrhythmia episode, such as a ventricular fibrillation, ventricular tachycardia, fast ventricular tachyarrhythmia episode, or a NST episode, based on electrocardiographic activity of the heart 12 that is monitored via sensing module 86. For example, the sensing module 86, with the aid of at least some of the electrodes 40, 42, 44, 46, 48, 50, 58, 62, 64, and 66 (shown in FIGS. 1-2), may generate an electrocardiogram (ECG) or electrogram (EGM) signal that indicates the electrocardiographic activity. Alternatively, the sensing module 86 may be coupled to sense electrodes that are separate from the stimulation electrodes that deliver electrical stimulation to the heart 12 (shown in FIGS. 1-3), and may be coupled to one or more different leads than leads 18, 20, 22 (shown in FIGS. 1-2). The ECG signal may be indicative of the depolarization of the heart 12.

For example, as previously described, in some examples, the processor 80 may identify the presence of a tachyarrhythmia episode by detecting a threshold number of tachyarrhythmia events (e.g., R-R or P-P intervals having a duration less than or equal to a threshold). In some examples, the processor 80 may also identify the presence of the tachyarrhythmia episode by detecting a variable coupling interval between the R-waves of the heart signal. In one example, the distal end of the lead 18 may be configured to be positioned in or on the His bundle and the IMB 16 may be configured to deliver pacing to stimulate the His bundle, during His bundle pacing, via electrodes 40 and 42, for example.

Figure 6:
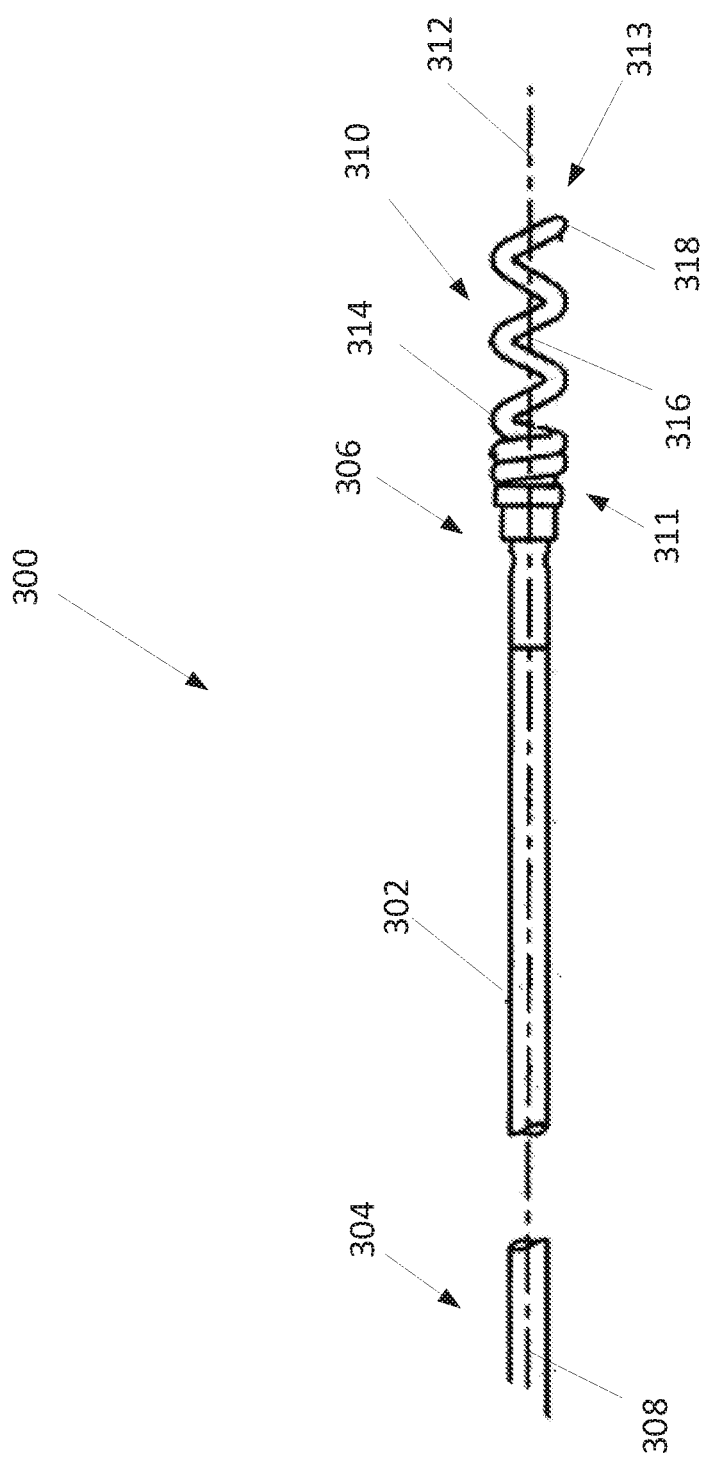
FIG. 6 is a plan view of an implantable medical lead including a helical fixation member for controlled bi-directional delivery of a therapeutic agent, according to an example of the present disclosure.

FIG. 6 is a plan view of an implantable medical lead including a helical fixation member for controlled bi-directional delivery of a therapeutic agent, according to an example of the present disclosure. As illustrated in FIG. 6, an implantable medical lead 300 according to an example of the present disclosure includes an elongated body 302 extending between a proximal end 304 and a distal end 306 along a longitudinal axis 308, which is an imaginary line running through a center of the elongated body 302 along an x-axis direction, i.e., from the proximal end 304 to the distal end 306. A connector assembly (not shown) is positioned at the proximal end 304 of the elongated body 302 to electrically connect the lead 300 to the connector block 34, shown above. An electrode in the form of a helical fixation member 310, for example, is attached to the lead body 302 and extends from the distal end 306 of the elongated lead body 302. In particular, helical fixation member 310 extends from a proximal end 311 to a distal end 313, with the proximal end 311 of helical fixation member 310 being wound about the distal end 306 of the lead body 302 to fixedly attached proximal end 311 of the helical fixation member 310 to the distal end 306 of the lead body 302.

Helical fixation member 310 actively fixates the distal end 306 of the elongated body 302 at a desired implant site. Helical fixation member 310 doubles as an electrode to which pacing pulses may be delivered, such as via pulse generator 84, and through which cardiac electrical function can be sensed, such as via sensing module 86. In one example, helical fixation member 310 may be a helix hollow electrode in the form of a helically wound capillary having an outer diameter of approximately 0.008-0.015" and an inner diameter of approximately 0.004". Materials for forming the helical fixation member 310 include, but are not limited to a pure tantalum or platinum-iridium alloy, and may be coated with an electrically conductive coating of titanium nitride.

In the example shown in FIG. 6, the helical fixation member 310 is comprised of multiple turns that are concentric about a center axis 312, which is aligned with the longitudinal axis 308 of the elongated body 302. Helical fixation member 310 winds around the center axis 312 in a counterclockwise direction, thereby defining an outer surface 314 and an inner surface 316 of the helical fixation member 310. The outer surface 314 of the helical electrode 310 is configured to engage with a catheter (not shown), which may be used to guide the lead 300 to the desired implant site, while the inner surface 316 of the helical electrode 310 faces the center axis 312 and is configured to engage with a guide wire (not shown), which may be used to guide the lead 300 to the implant site. As known in the art, the guide wire may be used in addition to or instead of the catheter.

Helical fixation member 310 is configured to fixate the distal end 306 of elongated body 302 at a desired implant site. In order to accomplish this, the distal end 313 of helical fixation member 310 includes a tissue-piercing tip 318, which may be referred to as a "chisel-tip" because of its shape. In order to fixate the distal end 306 of the lead 300 at a desired implant site, the helical fixation member 310 is positioned at the desired implant site and rotated to "screw" tip 318 to pierce the surface tissue at the site, and after one or more turns of helical fixation member 310, advance the helical fixation member 310 further within tissue at the desired implant site, which may be, for example, cardiac vasculature. Mechanisms for moving the helical fixation member 310 are well known to those skilled in the art, but are typically activated by a rotating a connector pin that is located at the proximal end 304 of the lead 300. The tip 318 includes a sharp edge, which is used to facilitate the introduction of tip 318 into the desired implant site. While the remainder of the description below refers to cardiac vasculature or tissue and an implant site interchangeably, it should be understood that the implantable medical lead 300 in accordance with the present disclosure is also suitable for use with other implant sites within a body.

FIG. 7 is a schematic diagram of a helical fixation member for controlled bi-directional delivery of a therapeutic agent, according to an example of the present disclosure. As illustrated in FIG. 7, the helical fixation member 310 includes a proximal delivery port 320 and a distal delivery port 322, both of which are in fluid communication with a lumen 324 (partially shown in hashed line) within the helical fixation member 310 that extends from a proximal end 311 to a distal end 313 of the helical fixation member 310, and forms the inner diameter of the helical fixation member 310. In one example, both the proximal delivery port 320 and the distal delivery port 322 may have a diameter of approximately 0.0005-0.004". However, in some examples, the diameters of the proximal delivery port 320 and the distal delivery port 322 may have different values, as described below, for example.

As a result, once the helical fixation member 310 is fixated within tissue, such as cardiac tissue for example, a therapeutic agent, such as a steroid, may be bi-directionally released from the helical fixation member 310 within the cardiac tissue via the proximal delivery port 320 and the distal delivery port 322. More specifically, in order to enable a controlled bi-directional release of the therapeutic agent, the proximal delivery port 320 is space a distance 326 from the distal deliver port 322, with no additional deliver ports being positioned within the distance 326 that the distal delivery port 322 is spaced from the proximal delivery port 320. In one example, the steroid may be dexamethasone, beclomethasone, or its polymer mixture.

FIG. 8 is a schematic diagram of a helical fixation member for controlled bi-directional delivery of a therapeutic agent, according to an example of the present disclosure. As illustrated in FIG. 8, according to an example of the present disclosure, the distance 326 that the proximal delivery port 322 of the electrode 310 is spaced from the distal delivery port 322 is configured so that the proximal delivery port 320 of the electrode 310 is positioned within an endothelial layer 328 of the tissue, and the distal delivery port 322 is positioned within a layer of myocardial tissue 330 below the endothelial layer 328. For example, the distance 326 between the proximal delivery port 320 and the distal delivery port 322 may be in the range of 2 mm to 12 mm. In one example, the distance 326 between the proximal delivery port 320 and the distal delivery port 322 may be approximately 8 mm.

As a result, the electrode 310 of the present disclosure enables a more targeted and controlled delivery of the therapeutic agent 332 near the distal end 306 of the lead 300 along a top surface 336 of the cardiac tissue at the implant site and within the first fusion zone 334 located within the endothelial layer 328 of the tissue. In addition, the therapeutic agent 332 is delivered within a separate, second fusion zone 336 located at the distal end 313 of the helical electrode 310 and within the myocardial tissue 330 via the distal delivery port 322. Since the therapeutic agent 332 is not delivered directly from the electrode 310 to the myocardial tissue 330 along the space 326 between the proximal delivery port 320 and the distal delivery port 322, but rather is controlled so as to be delivered only within the first fusion zone 334 and the second fusion zone 338, the electrode 310 of the present disclosure is configured to deliver the therapeutic agent 332 using a more controlled, bi-directional release of the therapeutic agent 332.

In another example, the diameters of the proximal delivery port 320 and the distal delivery port 322 may have different values, enabling the amount of the therapeutic agent that is delivered via one delivery port to be different relative to the other port. For example, it may be desirable for the therapeutic agent to be delivered from the proximal delivery port 320 at a rate greater than the amount delivered from the distal delivery port 322, resulting in more of the agent being delivered to the first fusion zone 334 being greater than the amount of therapeutic agent delivered to the second fusion zone 336. Therefore, in this example the diameter of the proximal delivery port 320 would be configured to be greater than the diameter of the distal delivery port 322. In another example, it may be desirable for the therapeutic agent to be delivered from the proximal delivery port 320 at a rate less than the amount delivered from the distal delivery port 322, resulting in more of the agent being delivered to the second fusion zone 336 being greater than the amount of therapeutic agent delivered to the first fusion zone 334. Therefore, in this example the diameter of the proximal delivery port 320 would be configured to be less than the diameter of the distal delivery port 322.

By being configured to enable a more controlled, bi-directional release of a therapeutic agent 332, the present disclosure provides a more targeted and controlled approach to ensure that the therapeutic agent 332 is delivered to minimize the inflammatory response at specific targeted areas of tissue where inflammation is most likely to occur. For example, the present disclosure causes ensures that the therapeutic agent 332 is delivered within the endothelial layer 328 of the tissue located in an area where the distal end 306 of the lead 300 comes in contact with the top surface 336 of the cardiac tissue at the implant site. By enabling delivery of the therapeutic agent to be controlled so as to be delivered within two separate specific fusion zones 334 and 338, the total fusion area may be reduced and more targeted, thereby minimizing the amount of the therapeutic agent 332 that is delivered, extending the time period that the therapeutic agent 332 continues to be released and enabling a more controlled and targeted reduction in the inflammation that may occur.

In addition, such controlled bi-directional release of the present disclosure minimizes corruption in the strength of the electrode 310 that would occur if the number of delivery ports is increased to be more than the two delivery ports described, thereby increasing the ability of the electrode 310 to more easily penetrate the tissue at the implant site, and further reducing the amount of inflammation that occurs at specific selected targeted problem areas of the implant site. Furthermore, by having only the proximal delivery port 320 space the distance 326 from the distal deliver port 322, with no delivery ports located along the electrode 310 within the distance 326 between the proximal delivery port 320 and the distal deliver port 322, the delivery of a therapeutic agent according to the present disclosure simplifies capillary filling of the electrode 310.

Figure 9:
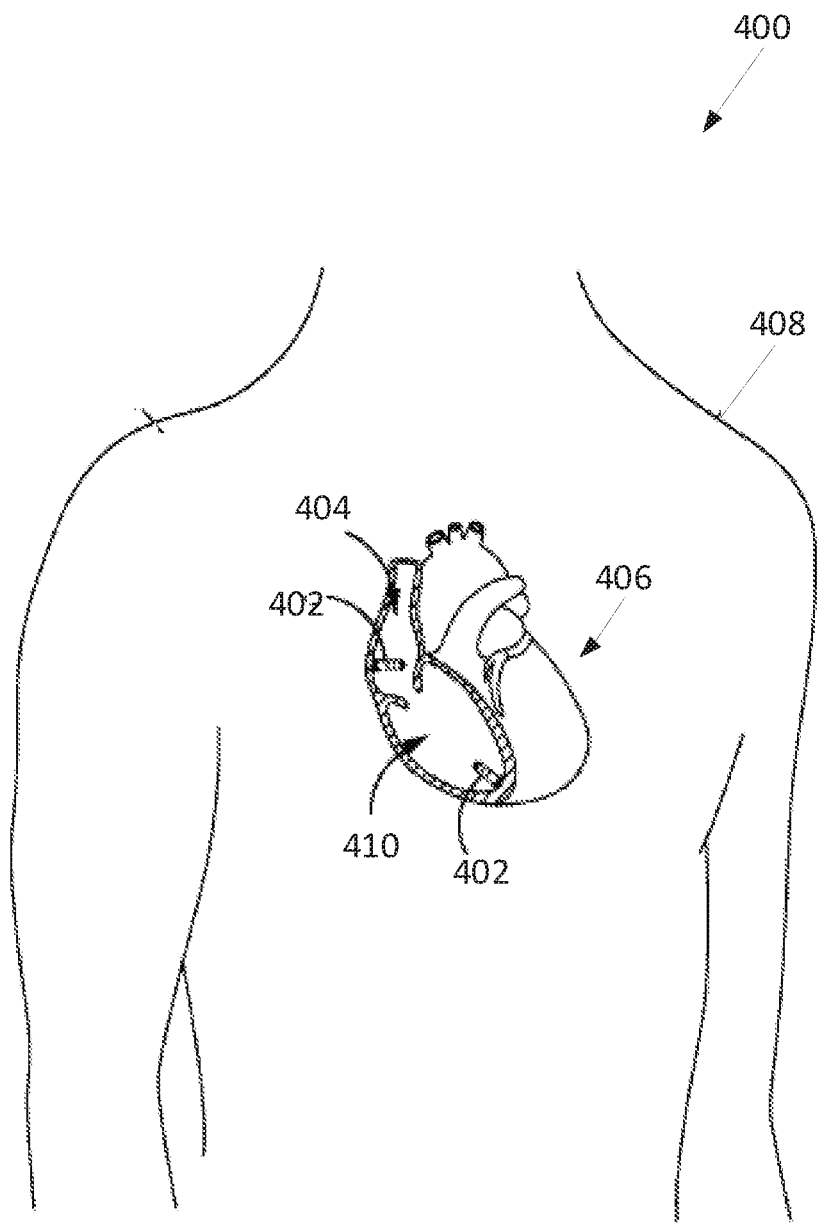
FIG. 9 is a conceptual diagram illustrating an example medical device system for delivering a therapeutic agent, consistent with an example of the present disclosure.

FIG. 9 is a conceptual diagram illustrating an example medical device system for delivering a therapeutic agent, consistent with an example of the present disclosure. As illustrated in FIG. 9, a system 400 having bi-directionally controlled release of a therapeutic agent according to the present disclosure may include one or more leadless pacemaker device 402 configured to be positioned within either a right atrium 404 of a heart 406 of a patient 408, within a right ventricle 410 of the patient 408, or both as illustrated in FIG. 9. The leadless pacemaker device 402 may be configured to monitor electrical activity of the patient's 408 heart 406 and/or provide electrical therapy to the heart 406.

Figure 10:
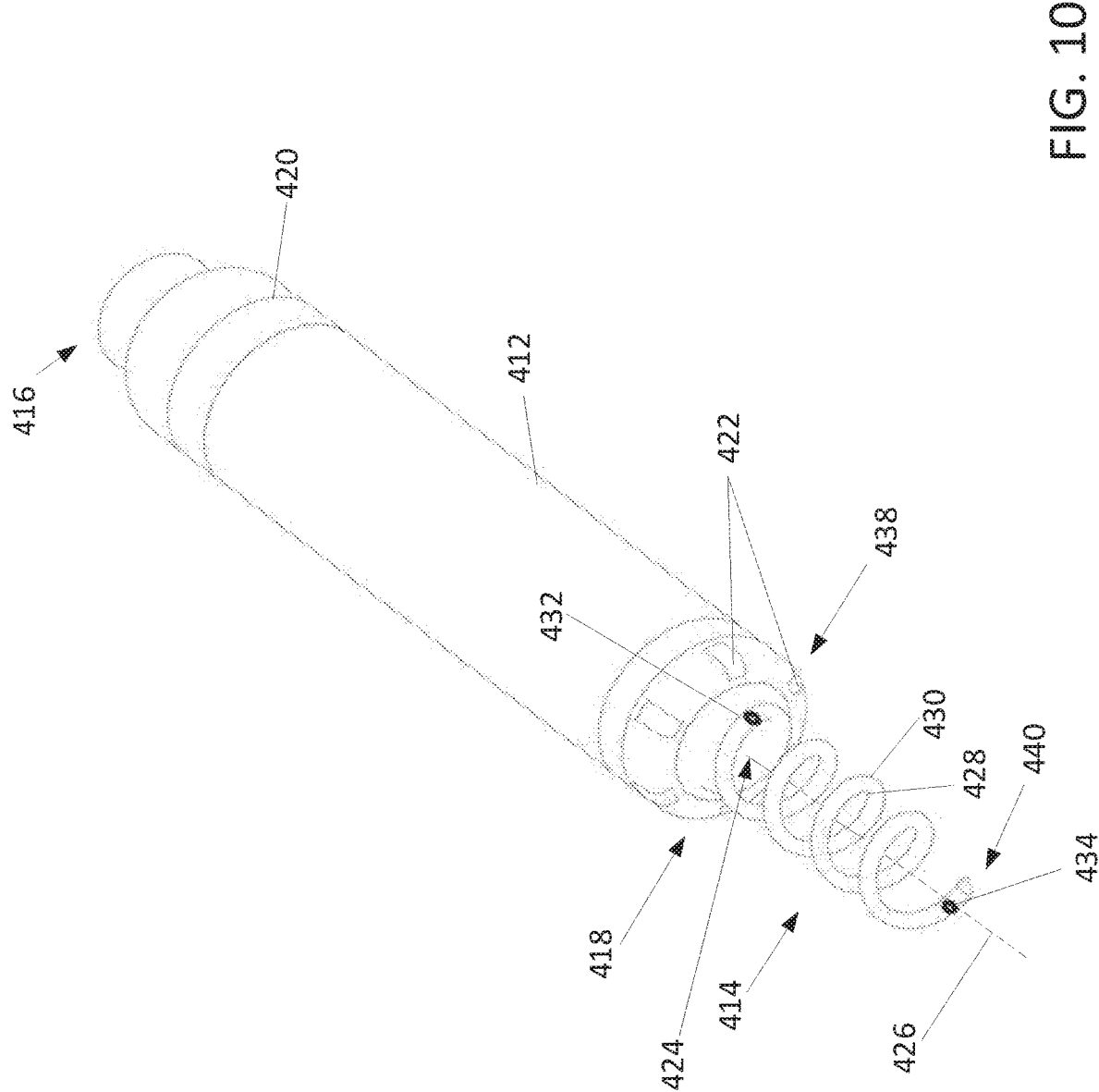
FIG. 10 is a conceptual diagram illustrating the example medical device of FIG. 9 according to an example of the present disclosure.

FIG. 10 is a conceptual diagram illustrating the example medical device of FIG. 9 according to an example of the present disclosure. As illustrated in FIG. 10, the leadless pacemaker device 402 includes a housing 412, and a helical fixation member 414, similar to the helical fixation member 310 described above, configured to connect (e.g., anchor) the leadless pacemaker device 402 to the heart 406. Housing 412, which may have a pill-shaped cylindrical form factor in some examples, extends from a proximal end 416 to a distal end 418. In addition, the leadless pacemaker device 402 includes a ring electrode 420 positioned at the proximal end 416 of the housing 412, and one or more tip electrodes 422 positioned at the distal end 418 of the housing 412. In this way the ring electrode 420 and tip electrodes 422 may be utilized by the leadless pacemaker device 420 for sensing electrical activity of the heart 406 and/or delivering electrical stimulation to heart 406. The ring electrode 420 and tip electrodes 422 may be spaced apart a sufficient distance to be able to detect various electrical signals generated by the heart 406, such as P-waves generated by atria and R-waves generated by the ventricles. In one embodiment, for example, the ring electrode 420 and tip electrodes 422 may be spaced at least 17 mm apart from one another. Although the ring electrode 420 is illustrated as a cylindrical electrode that wraps around the housing 412, the ring electrode 420 may include other geometries. In addition, while the leadless pacemaker device 402 illustrated in FIG. 10 includes multiple electrodes tip electrodes 422, in another embodiment the leadless pacemaker device may include only a single electrode (not shown) centrally located at an area 424 of the distal end 418 of the housing 412. In some examples, the housing 412 may be formed from a conductive material. In these examples, the housing 412 may act as an electrode of the leadless pacemaker device 402. In addition, in some examples, the helical fixation member 414 may form an active electrode, or include an active electrode formed thereon, such as having an active electrode positioned along a distal end 440 of the helical fixation member 414, for example, and may be utilized for multi-site leadless pacing.

The housing 412 houses electronic components of the leadless pacemaker device 402. Electronic components may include any discrete and/or integrated electronic circuit components that implement analog and/or digital circuits capable of producing the functions attributed to the leadless pacemaker device 402 described herein. For example, the housing 412 may house electronic components that sense electrical activity via the ring electrode 420 and tip electrodes 422 and/or deliver electrical stimulation via the ring electrode 420 and tip electrodes 422. Additionally, the housing 412 may also include memory that includes instructions that, when executed by one or more processing circuits housed within the housing 412, cause the leadless pacemaker device 402 to perform various functions attributed to the leadless pacemaker device 402. The housing 412 may also house sensors that sense physiological conditions of the patient 408, such as an accelerometer and/or a pressure sensor.

In some examples, the housing 412 may house a communication module that enables the leadless pacemaker device 402 to communicate with other electronic devices, such as a programmer or other external patient monitor. In some examples, the housing 412 may house an antenna for wireless communication. The housing 412 may also include a power source, such as a battery. Electronic components included within the housing 412 are described in further detail hereinafter.

Similar to the helical fixation member 310 described above, the helical fixation member 414 winds around a center axis 426 in a counterclockwise direction, and includes an inner surface 428 that faces the center axis 426 and an outer surface 430 that faces the outer area surrounding the helical fixation member 414. The helical fixation member 414 includes a proximal delivery port 432 and a distal delivery port 434, both of which are in fluid communication with a lumen 424 (shown in FIG. 7) within the helical fixation member 414 that extends from a proximal end 438 to the distal end 440 of the helical fixation member 414 and forms the inner diameter of the helical fixation member 414. In one example, both the proximal delivery port 432 and the distal delivery port 434 may have a diameter of approximately 0.0005-0.004". However, in some examples, the diameters of the proximal delivery port 432 and the distal delivery port 434 may have different values, as described below, for example. In either the case, i.e., the diameters being the same or the diameters being different, according to one example, the total of the two diameters may be less than or equal to a diameter of the lumen 324 of the fixation member 310.

As a result, once the helical fixation member 414 is fixated within tissue, such as cardiac tissue for example, a therapeutic agent, such as a steroid, may be bi-directionally released from the helical fixation member 414 within the cardiac tissue via the proximal delivery port 432 and the distal delivery port 434. More specifically, in order to enable a controlled bi-directional release of the therapeutic agent, the proximal delivery port 432 is space a distance from the distal deliver port 434, similar to the distance 326 described above, with no additional deliver ports being positioned within the distance that the distal delivery port 434 is spaced from the proximal delivery port 432. As described above, the distance that the proximal delivery port 432 is spaced from the distal delivery port 434 is configured so that the proximal delivery port 432 is positioned within an endothelial layer 328 of the tissue, and the distal delivery port 434 is positioned within a layer of myocardial tissue 330 below the endothelial layer 328. For example, the distance between the proximal delivery port 432 and the distal delivery port 434 may be in the range of 2 mm to 12 mm. In one example, the distance between the proximal delivery port 432 and the distal delivery port 434 may be approximately 8 mm. In one example, the steroid may be dexamethasone, beclomethasone, or its polymer mixture.

In one example in which the tip electrodes 422 are positioned around the distal end 418 of the housing 412 and outside of the helical fixation member 414, as shown in FIG. 10, the proximal delivery port 432 may be configured to be located along the outer surface 430 of the helical fixation member 414 in order to control the delivery of the therapeutic agent so as to be released along the tip electrodes 422.

However, in another example in which a single electrode is centrally located along the area 424 of the distal end 418 of the housing 412, the proximal delivery port 432 may be configured to be located along the inner surface 428 of the helical fixation member 414 in order to control the delivery of the therapeutic agent so as to be released along the tip electrode.

In addition, as described above, the diameters of the proximal delivery port 432 and the distal delivery port 434 may be the same, or may have different values, enabling the amount of the therapeutic agent that is delivered via one delivery port to be different relative to the other port. For example, the diameter of the proximal delivery port 432 may be configured so as to be greater than the diameter of the distal delivery port 434 so that therapeutic agent may be delivered from the proximal delivery port 432 at a rate greater than the amount delivered from the distal delivery port 434, resulting in more of the agent being delivered along the tip electrodes 422 and/or within the first fusion zone 334 being greater than the amount of therapeutic agent delivered along the distal end 440 of the helical fixation member 414 and/or the second fusion zone 336. Therefore, in this example the diameter of the proximal delivery port 432 would be configured to be greater than the diameter of the distal delivery port 434. In either the case, i.e., the diameters of the proximal delivery port 432 and the distal delivery port 434 being the same or the diameters of the proximal delivery port 432 and the distal delivery port 434 being different, according to one example, the total of the diameters of the proximal delivery port 432 and the distal delivery port 434 are configured to be less than or equal to a diameter of the lumen 436 of the fixation member 414.

Figure 11:
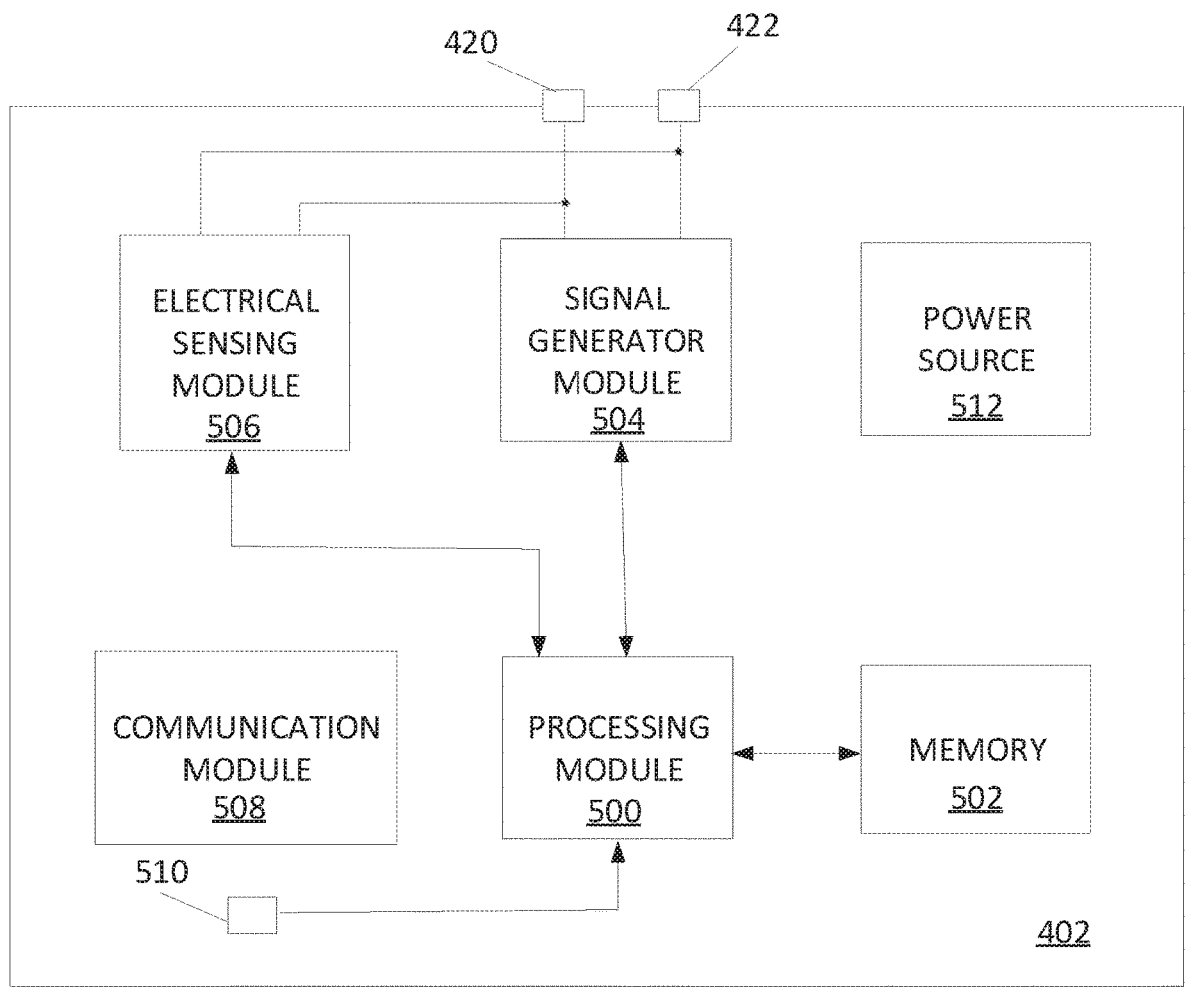
FIG. 11 is a functional block diagram of an example configuration of a leadless pacemaker device according to an example of the present disclosure.

FIG. 11 is a functional block diagram of an example configuration of a leadless pacemaker device according to an example of the present disclosure. As illustrated in FIG. 11, the leadless pacemaker device 402 may include a processing module 500, a memory 502, a signal generator module 504, an electrical sensing module 506, a communication module 508, a sensor 510, and a power source 512. The power source 512 may include a battery, e.g., a rechargeable or non-rechargeable battery.

Modules included in the leadless pacemaker device 402 represent functionality that may be included in atrial device 100 of the present disclosure. As discussed in U.S. Patent Application Pub. No. 2014/0121720, incorporated herein by reference, similar or identical modules and functionality may also be included in a ventricular pacemaker device, which may be provided as part of a dual-chamber, leadless pacemaker system for implantation and use in at least one atrium and at least one ventricle of a heart. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects, and does not necessarily imply that such modules must be realized by separate hardware or software components. Rather, functionality associated with one or more modules may be performed by separate hardware or software components, or integrated within common or separate hardware or software components.

The processing module 500 may communicate with the memory 502. The memory 502 may include computer-readable instructions that, when executed by the processing module 500, cause the processing module 500 to perform the various functions attributed to the processing module 500 herein. The memory 502 may include any volatile, non-volatile, magnetic, or electrical media, such as RAM, ROM, NVRAM, EEPROM, Flash memory, or any other digital media. For example, the memory 502 may include pacing instructions and values, such as the baseline atrial pacing rate, the baseline atrial pacing interval and the baseline AV interval. The pacing instructions and values may be updated by a programmer. Pacing instructions included in the memory 502 may cause the leadless pacing device 402 to operate as described in U.S. Patent Application Pub. No. 2014/0121720, which was previously incorporated by reference.

The processing module 500 may communicate with the signal generator module 504 and the electrical sensing module 506. The signal generator module 504 and the electrical sensing module 506 are electrically coupled to the ring electrode 420 and the tip electrodes 422. The electrical sensing module 506 is configured to monitor signals from the ring electrode 420 and the tip electrodes 422 in order to monitor electrical activity of the heart 406. The signal generator module 504 is configured to deliver electrical stimulation to the 404 via the ring electrode 420 and the tip electrodes 422.

The processing module 500 may control the signal generator module 504 to generate and deliver electrical stimulation to the atrium 404 via the ring electrode 420 and the tip electrodes 422. Electrical stimulation may include pacing pulses. The processing module 500 may control the signal generator module 504 to deliver electrical stimulation therapy according to one or more atrial therapy programs including pacing instructions and values, which may be stored in the memory 502.

The electrical sensing module 506 may include circuits that acquire electrical signals. Electrical signals acquired by the electrical sensing module 506 may include intrinsic cardiac electrical activity, such as intrinsic atrial and/or intrinsic ventricular cardiac electrical activity. The electrical sensing module 506 may filter, amplify, and digitize the acquired electrical signals to generate raw digital data. The processing module 500 may receive the digitized data generated by the electrical sensing module 506. In some examples, the processing module 500 may perform various digital signal processing operations on the raw data, such as digital filtering.

The processing module 500 may sense cardiac events based on the data received from the electrical sensing module 506. For example, the processing module 500 may sense atrial events based on the data received from the electrical sensing module 506. In some examples, the processing module 500 may sense ventricular activation based on the data received from the electrical sensing module 506. For example, the processing module 500 may detect R-waves indicative of ventricular activation based on the data received from the electrical sensing module 506.

By being configured to enable a more controlled, bi-directional release of a therapeutic agent, the present disclosure provides a more targeted and controlled approach to ensuring that the therapeutic agent is delivered to minimize the inflammatory response at specific targeted areas of tissue where inflammation is most likely to occur, such as within the endothelial layer of the tissue located in an area where the tip electrodes 422 come in contact with the top surface 336 of the cardiac tissue at the implant site. By enabling delivery of the therapeutic agent to be controlled so as to be delivered within two separate specific fusion zones 334 and 338, the total fusion area may be reduced and more targeted, thereby minimizing the amount of the therapeutic agent 332 that is delivered, extending the time period that the therapeutic agent 332 continues to be released and enabling a more controlled and targeted reduction in the inflammation that may occur.

In addition, such controlled bi-directional release of the present disclosure minimizes corruption in the strength of the helical fixation member 414 that would occur if the number of delivery ports is increased to be more than the two delivery ports described, thereby increasing the ability of the helical fixation member 414 to more easily penetrate the tissue at the implant site, and further reducing the amount of inflammation that occurs at specific selected targeted problem areas of the implant site. Furthermore, by having only the proximal delivery port 432 space the distance from the distal deliver port 434, with no delivery ports located along the helical fixation member 414 within the distance between the proximal delivery port 432 and the distal deliver port 434, the delivery of a therapeutic agent according to the present disclosure simplifies capillary filling of the helical fixation member 414.

All references and publications cited herein are expressly incorporated herein by reference in their entirety into this disclosure, except to the extent they may directly contradict this disclosure. Illustrative embodiments of this disclosure are discussed, and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. An implantable medical lead, comprising:
    an elongated lead body extending from a proximal end to a distal end;
    a helical fixation member having a proximal end and a distal end, the proximal end of the helical fixation member configured to be coupled to and extending from the distal end of the lead body, the helical fixation member comprising:
        a first delivery port and a second delivery port for releasing a therapeutic agent from the helical fixation member to tissue of a patient, wherein the first delivery port is positioned along the proximal end of the helical fixation member to deliver the therapeutic agent to endothelial cells along an endothelial layer of tissue when the distal end of the lead body is in contact with a top surface of the tissue of the patient, and the second delivery port is positioned along the distal end of the helical fixation member and spaced a distance from the first delivery port to deliver the therapeutic agent to myocardial tissue within a myocardial layer of the tissue, and wherein no delivery ports are positioned within the distance that the second delivery port is spaced from the first delivery port.

2. The implantable medical lead of claim 1, wherein the first delivery port has a first diameter and the second delivery port has a second diameter, and wherein the first diameter is approximately equal to the second diameter.

3. The implantable medical lead of claim 1, wherein the first delivery port has a first diameter and the second delivery port has a second diameter, and wherein the first diameter is greater than the second diameter.

4. The implantable medical lead of claim 1, wherein the first delivery port has a first diameter and the second delivery port has a second diameter, and wherein the first diameter is less than the second diameter.

5. The implantable medical lead of claim 1, wherein the helical fixation member comprises an electrode for at least one of sensing a cardiac signal and delivering a cardiac therapy.

6. The implantable medical lead of claim 1, wherein the distance is in the range of 2 millimeters to 12 millimeters.

7. An implantable medical device, comprising:
a housing extending from a proximal end to a distal end;
a sensing module within the housing to sense a cardiac signal;
a stimulation generator within the housing to deliver a cardiac therapy in response to the sensed cardiac signal; and
a fixation member having a proximal end and a distal end, the proximal end of the fixation member coupled to and extending from a distal end of the housing, the fixation member comprising:
a first delivery port and a second delivery port for releasing a therapeutic agent from the fixation member to tissue of a patient, wherein the first delivery port is positioned along the proximal end of the fixation member to deliver the therapeutic agent to endothelial cells along an endothelial layer of tissue when the distal end of the housing is in contact with a top surface of the tissue of the patient, and the second delivery port is positioned along the distal end of the fixation member and spaced a distance from the first delivery port to deliver the therapeutic agent to myocardial tissue within a myocardial layer of the tissue, and wherein no delivery ports are positioned within the distance that the second delivery port is spaced from the first delivery port.

8. The implantable medical device of claim 7, wherein the implantable medical device comprises a leadless pacemaker device.

9. The implantable medical device of claim 7, wherein the first delivery port has a first diameter and the second delivery port has a second diameter, and wherein the first diameter is approximately equal to the second diameter.

10. The implantable medical device of claim 7, wherein the first delivery port has a first diameter and the second delivery port has a second diameter, and wherein the first diameter is greater than the second diameter.

11. The implantable medical device of claim 7, wherein the first delivery port has a first diameter and the second delivery port has a second diameter, and wherein the first diameter is less than the second diameter.

12. The implantable medical device of claim 7, wherein the fixation member comprises a helical fixation member, and the implantable medical device further comprises:

one or more electrodes for at least one of sensing a cardiac signal and delivering a cardiac therapy positioned at the distal end of the housing, wherein the first delivery port is positioned along an outer surface of the helical fixation member and the one or more electrodes are positioned outside of the helical fixation member.

13. The implantable medical device of claim 7, wherein the fixation member comprises a helical fixation member having an inner surface and an outer surface, and wherein both the first delivery port and the second delivery port are positioned along one of the inner surface and the outer surface the helical fixation member.

14. The implantable medical device of claim 7, wherein the fixation member comprises a helical fixation member having an inner surface and an outer surface, and wherein the first delivery port is positioned along the outer surface of the helical fixation member and the second delivery port is positioned along the inner surface of the helical fixation member.

15. The implantable medical device of claim 14, wherein first delivery port has a first diameter and the second delivery port has a second diameter, and wherein the first diameter is greater than the second diameter.

16. The implantable medical device of claim 7, wherein the fixation member comprises a helical fixation member and the implantable medical device further comprises:
an electrode for at least one of sensing a cardiac signal and delivering a cardiac therapy positioned at the distal end of the housing, wherein the first delivery port is positioned along an inner surface of the helical fixation member and the electrode is positioned within the helical fixation member.

17. A fixation member for use with an implantable medical device extending from a distal end of a lead body or housing, the fixation member comprising:
a helical body having a proximal end and a distal end and configured to be fixedly position within cardiac tissue;
a lumen extending within the helical body and extending from the proximal end to the distal end;
a first delivery port positioned along the proximal end of the helical body and in fluid communication with the lumen to deliver a therapeutic agent within the lumen to the cardiac tissue; and
a second delivery port positioned along the distal end of the helical body and in fluid communication with the lumen to deliver the therapeutic agent to the cardiac tissue, the second delivery port spaced a distance from the first delivery port so that, when the distal end of the lead body or housing is in contact with a top surface of the tissue of the patient, the therapeutic agent is delivered via the first delivery port to endothelial cells along an endothelial layer of the cardiac tissue, and the therapeutic agent is delivered via the second delivery port to myocardial tissue within a myocardial layer of the cardiac tissue, and wherein no delivery ports are positioned within the spaced distance between the first delivery port and the second delivery port.

18. The fixation member of claim 17, where first delivery port has a first diameter and the second delivery port has a second diameter, and wherein the first diameter is approximately equal to the second diameter.

19. The fixation member of claim 17, wherein the first delivery port has a first diameter and the second delivery port has a second diameter, and wherein the first diameter is greater than the second diameter.

20. The fixation member of claim 17, wherein the first delivery port has a first diameter and the second delivery port has a second diameter, and wherein the first diameter is less than the second diameter.

21. The fixation member of claim 17, wherein the fixation member comprises an electrode for at least one of sensing a cardiac signal and delivering a cardiac therapy.

22. The fixation member of claim 17, wherein the fixation member comprises a helical fixation member.

* * * * *